US012570101B2

(12) United States Patent (10) Patent No.: US 12,570,101 B2
Moriyama et al. (45) Date of Patent: Mar. 10, 2026

(54) RECORDING DEVICE

(71) Applicant: SEIKO EPSON CORPORATION, Tokyo (JP)

(72) Inventors: Ryuji Moriyama, Matsumoto (JP); Yoshihiko Momose, Shiojiri (JP); Yoichi Kobayashi, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 122 days.

(21) Appl. No.: 18/434,250

(22) Filed: Feb. 6, 2024

(65) Prior Publication Data

US 2024/0262115 A1 Aug. 8, 2024

(30) Foreign Application Priority Data

Feb. 7, 2023 (JP) ................................. 2023-016794

(51) Int. Cl.
*B41J 29/17* (2006.01)
*A61L 2/10* (2006.01)
*B41J 29/13* (2006.01)

(52) U.S. Cl.
CPC ................. *B41J 29/17* (2013.01); *A61L 2/10* (2013.01); *B41J 29/13* (2013.01)

(58) Field of Classification Search
None
See application file for complete search history.

(56) References Cited

U.S. PATENT DOCUMENTS

2019/0299660 A1* 10/2019 Matsunaga .............. B41J 29/13
2020/0207127 A1* 7/2020 Fujisawa .................. B41J 11/06
2021/0318654 A1* 10/2021 Takenaka ............. G03G 15/502
2023/0180958 A1* 6/2023 Kim ......................... A23N 1/02
99/493

FOREIGN PATENT DOCUMENTS

JP 2018-140530 A 9/2018

* cited by examiner

*Primary Examiner* — Alejandro Valencia
(74) *Attorney, Agent, or Firm* — WORKMAN NYDEGGER

(57) ABSTRACT

Provided is a recording device including a medium support portion that supports a medium, a recording unit that performs recording on the medium, an irradiation unit that emits an ultraviolet ray toward the medium, a deodorization portion that performs deodorization, and a housing that accommodates the medium support portion, the recording unit, the irradiation unit, and the deodorization portion, in which the deodorization portion includes a deodorization body, a deodorization body cover that covers the deodorization body, and an accommodation portion that accommodates the deodorization body covered by the deodorization body cover, and the deodorization body is configured to be taken out from the accommodation portion together with the deodorization body cover.

4 Claims, 9 Drawing Sheets

RECORDING DEVICE

The present application is based on, and claims priority from JP Application Serial Number 2023-016794, filed Feb. 7, 2023, the disclosure of which is hereby incorporated by reference herein in its entirety.

BACKGROUND

1. Technical Field

The present disclosure relates to a recording device.

2. Related Art

In the related art, in a recording device that records a character and an image, there has been known a recording device having a function of removing an odor caused by a recording material. For example, JP-A-2018-140530 discloses a printing device including a printing unit, a housing that accommodates the printing unit, and a gas cleaning unit that cleans gas. The gas cleaning unit is located outside the housing and communicates with the inside of the housing via a discharge unit and a supply unit. In this printing device, the odor of the gas inside the housing is decomposed or removed using a deodorant such as activated carbon or an ozone oxidant.

In the configuration in which the odor is decomposed or removed using the deodorant, it is necessary to replenish or replace a material used for deodorization in order to maintain a deodorization effect. Therefore, it has been desired to facilitate replenishment and replacement of the material used for deodorization.

SUMMARY

According to an aspect of the present disclosure, there is provided is a recording device including a medium support portion that supports a medium, a recording unit that performs recording on the medium, an irradiation unit that emits an ultraviolet ray toward the medium, a deodorization portion that performs deodorization, and a housing that accommodates the medium support portion, the recording unit, the irradiation unit, and the deodorization portion, in which the deodorization portion includes a deodorization body, a deodorization body cover that covers the deodorization body, and an accommodation portion that accommodates the deodorization body covered by the deodorization body cover, and the deodorization body is removable from the accommodation portion together with the deodorization body cover.

DESCRIPTION OF EMBODIMENTS

1. Configuration of Recording Device

Figure 1:
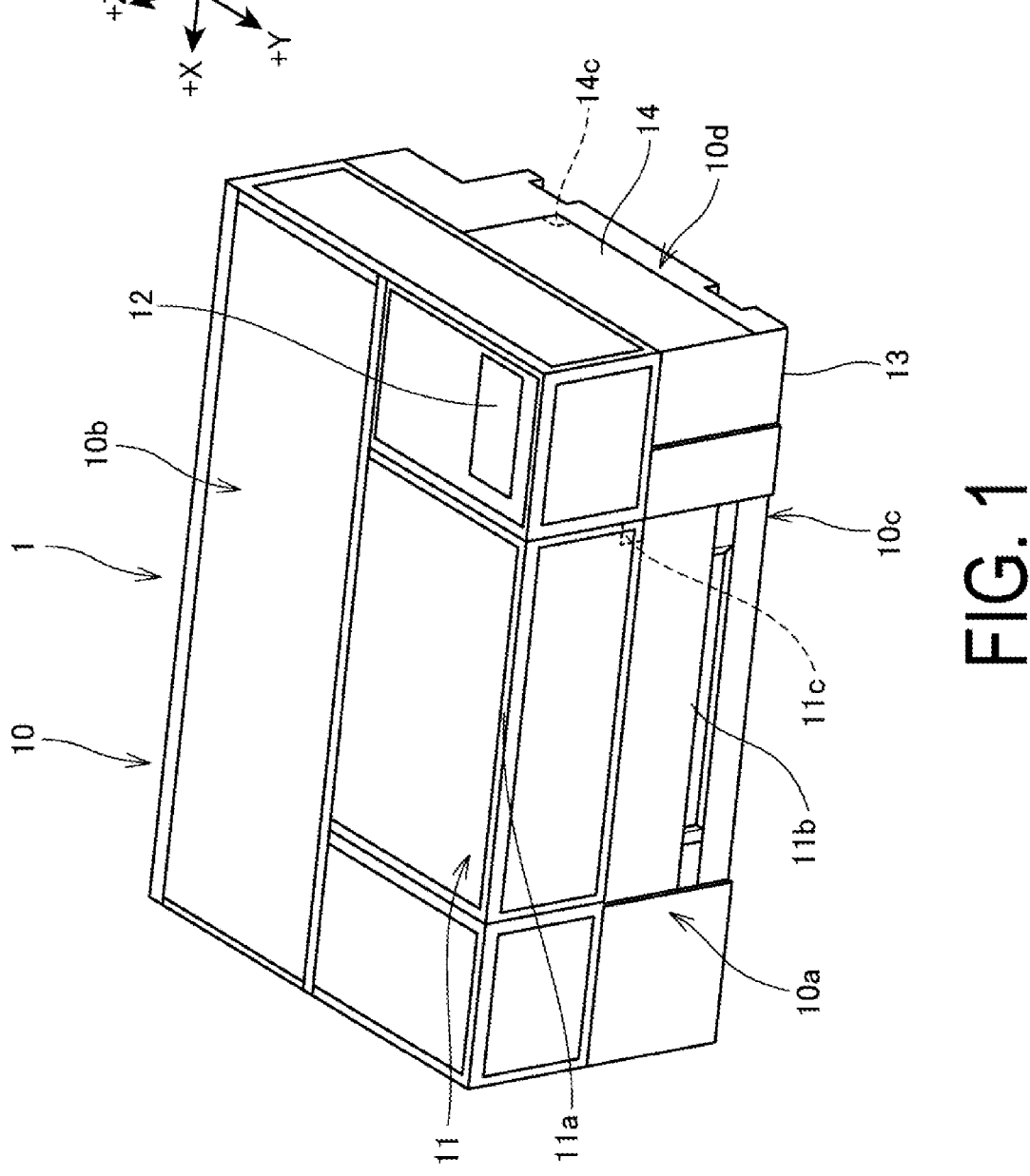
FIG. 1 is a perspective view of a recording device according to an embodiment.

FIG. 1 is a perspective view of a recording device 1 according to an embodiment. The recording device 1 is a device that performs recording on a medium M supported by a medium support portion 30, by ejecting a liquid from a recording head 89a. The medium M is a sheet, a cloth, or a three-dimensional object. The sheet may be a sheet made of paper or synthetic resin. The cloth may be any of a non-woven cloth, a knitted material, and a fabric. The three-dimensional object includes ornaments such as clothes or shoes, daily necessities, mechanical components, and other various objects. The type of liquid ejected onto the medium M by the recording device 1 is not limited, as long as the liquid has fluidity. For example, the recording device 1 is a printer that forms an image on the medium M by discharging ink of one or a plurality of colors toward the surface of the medium M by using the recording head 89a. In this case, the medium M can be referred to as a printing medium.

In FIG. 1, an X-axis, a Y-axis, and a Z-axis are illustrated. The X-axis, the Y-axis, and the Z-axis are orthogonal to one another. The Z-axis is an axis extending in an up-down direction, and can also be referred to as an axis extending in a vertical direction. The X-axis and the Y-axis are parallel to a horizontal plane. In the following description, a direction along the X-axis is referred to as a left-right direction, and a direction along the Y-axis is referred to as a front-rear direction. Specifically, a forward direction along the Z-axis is an upward direction, a forward direction along the X-axis is a rightward direction, and a forward direction along the Y-axis is a front direction. The forward direction corresponds to an example of a first direction. The X-axis corresponds to an example of a first axis. The Y-axis corresponds to an example of a second axis. The Z-axis is an axis corresponding to an example of a third axis and extending in the vertical direction in the installation state of the recording device 1.

The recording device 1 includes a housing 10. The housing 10 is a substantially cuboid box, and forms a closed space therein. The housing 10 covers the medium support portion 30, the recording head 89a, an irradiation unit 89b, a first deodorization portion 20, and a second deodorization portion 50, and the like, which will be described later, and accommodates these components in the closed space. The housing 10 includes a front surface cover 11 along a front surface 10a and an upper surface 10b. The front surface cover 11 includes a cover body 11a along the front surface 10a and the upper surface 10b, and a handle 11b coupled to the lower end of the cover body 11a. At the rear end of the cover body 11a, the front surface cover 11 is coupled to the upper surface 10b of the housing 10 by a hinge (not illustrated) so as to be rotatable about an axis in the left-right direction. Thus, the front surface cover 11 can be opened and closed from the front side by moving the handle 11b in the up-down direction. Furthermore, a bottom surface 10c of the housing 10 includes a bottom plate 13 which is a plate facing the installation surface of the housing 10. The installation surface is a surface on which the housing 10 is installed, such as a top surface of a desk (not illustrated).

The recording device 1 includes a touch panel 12 disposed at a front portion of the upper surface 10b. For example, the touch panel 12 is constituted by a liquid crystal panel and an LED. The touch panel 12 is coupled to a control unit 101 installed inside the housing 10. The touch panel 12 is constituted by overlapping a touch sensor that detects a contact operation on the surface of the touch panel 12 and a display panel. The display panel of the touch panel 12 is, for example, a liquid crystal panel. The control unit 101 controls the display panel of the touch panel 12 to display characters and images. Furthermore, the control unit 101 detects the contact operation on the touch panel 12 and specifies an operation position of the contact operation. The control unit 101 causes the touch panel 12 to display information regarding the progress of recording by the recording device 1 and the remaining amount of a liquid to be ejected during the recording. Furthermore, the control unit 101 displays information related to replacement times of consumables of the first deodorization portion 20 and the second deodorization portion 50, which will be described below. The control unit 101 causing the touch panel 12 to display information is an example of notification, and the touch panel 12 corresponds to an example of a notification unit.

Figure 2:
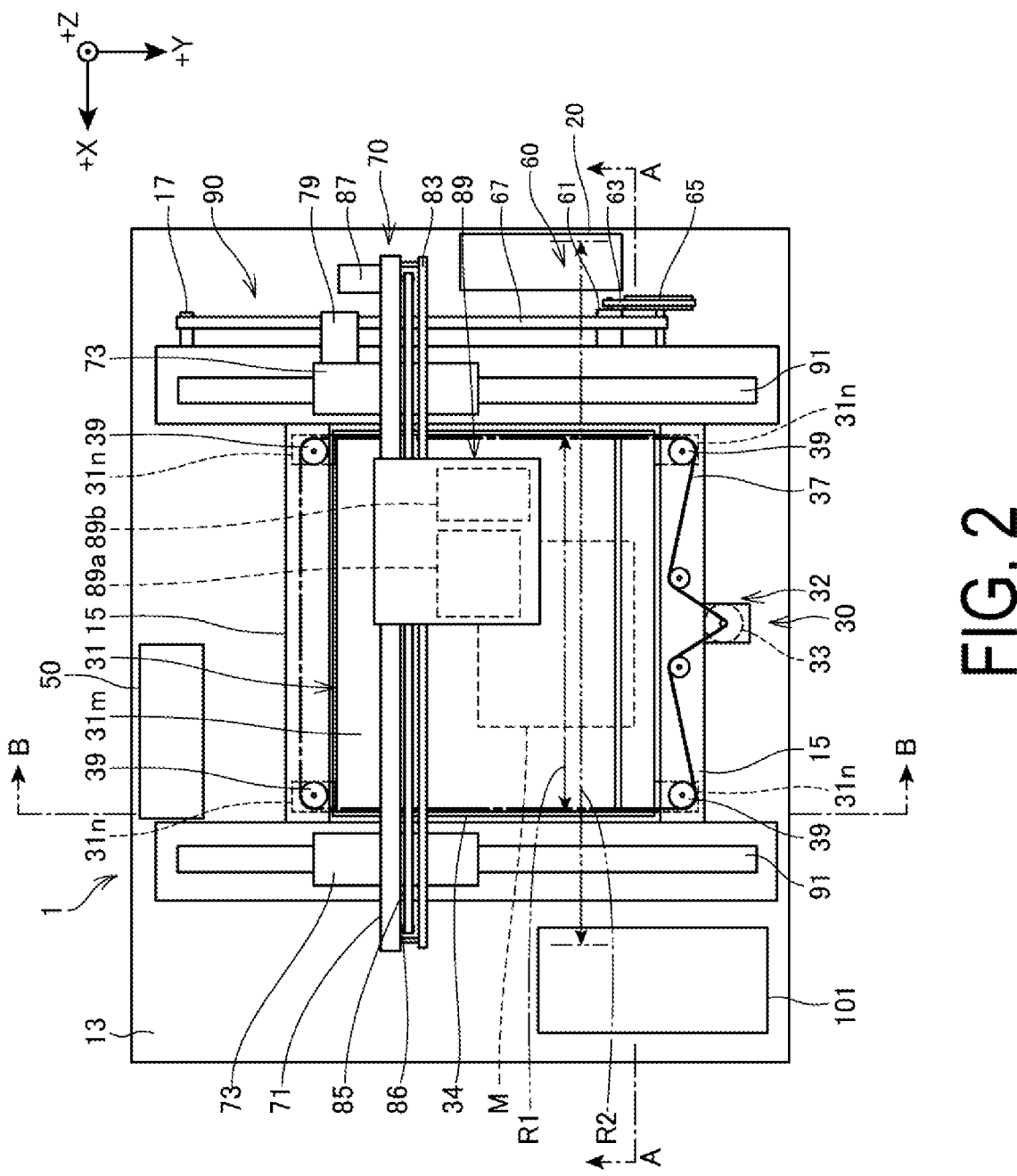
FIG. 2 is a plan view of a recording device.
Figure 3:
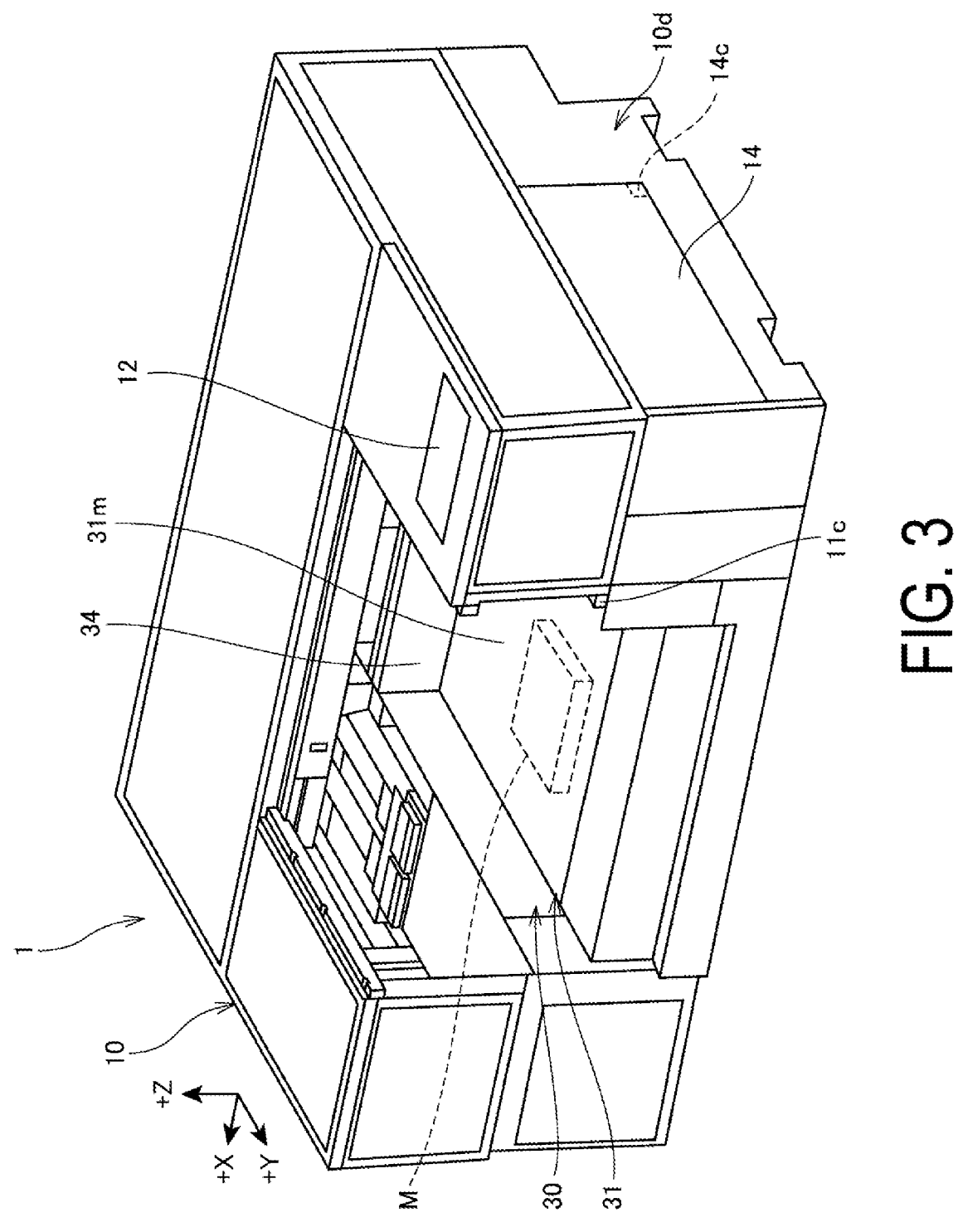
FIG. 3 is a perspective view of a recording device.

FIG. 2 is a plan view of the recording device 1 and schematically illustrates an internal structure of the recording device 1. FIG. 3 is a perspective view of the recording device 1. FIG. 3 illustrates a state in which the front surface cover 11 is removed for convenience of description.

As illustrated in FIG. 2, the recording device 1 includes a pair of base members 15, a pair of guide shafts 91, the first deodorization portion 20, the medium support portion 30, the second deodorization portion 50, a driving mechanism 90, and a movement unit 70. Each of the base members 15 is a member extending in the left-right direction. The two base members 15 are arranged side by side in the front-rear direction on the bottom plate 13, and are fixed to the bottom plate 13. Each of the guide shafts 91 is a shaft extending in the front-rear direction, and the two guide shafts 91 are respectively arranged side by side in the left-right direction so as to straddle the two base members 15.

The first deodorization portion 20 and the second deodorization portion 50 suck air inside the housing 10 and remove an odor contained in the sucked air to deodorize the air and discharge the air to the outside of the housing 10. Details of the first deodorization portion 20 and the second deodorization portion 50 will be described later.

Figure 4:
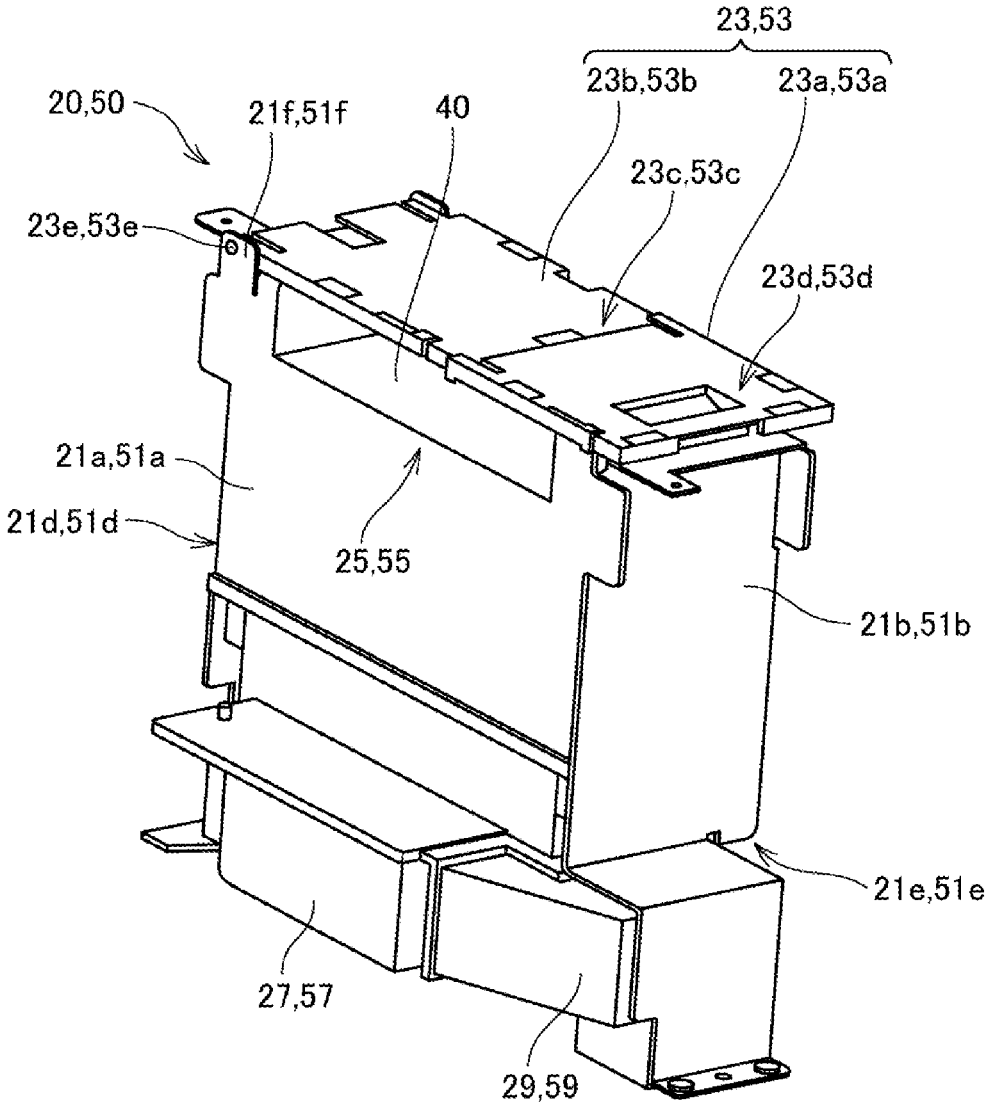
FIG. 4 is a perspective view of a deodorization portion.

The medium support portion 30 supports the medium M which is a recording target in the recording device 1. As illustrated in FIGS. 2 to 4, the medium support portion 30 includes a table 31, a fall prevention plate 34, and a height moving mechanism 32. The table 31 is disposed at a position surrounded by a pair of the base members 15 and a pair of the guide shafts 91 in plan view. The table 31 includes a support surface 31m which is a rectangular surface extending along the X-axis and the Y-axis, and facing upward.

The support surface 31m is a surface on which the medium M is placed in the medium support portion 30, and supports the medium M placed at the support surface 31m. As illustrated in FIG. 3, in a state in which the front surface cover 11 is opened, the support surface 31m is exposed to the front side and the upper side of the housing 10. Therefore, in a state in which the front surface cover 11 is opened, the medium M outside the housing 10 can be set on the support surface 31m of the medium support portion 30 from the front side of the support surface 31m. Furthermore, in a state in which the front surface cover 11 is opened, the medium M placed on the support surface 31m of the medium support portion 30 can be taken out at the outside of the housing 10.

The table 31 includes protruding portions 31n protruding outward from the support surface 31m in plan view, at lower portions of four corners of the support surface 31m. The table 31 is supported so as to be movable up and down with respect to the base members 15 by fixing the protruding portions 31n to lifting mechanisms 39 to be described later.

The fall prevention plate 34 is a plate member that is vertically erected in contact with the left side, the right side, and the rear side of the support surface 31m. In other words, the fall prevention plate 34 is perpendicular to the support surface 31m and surrounds the support surface 31m in the left-right direction and on the rear side along the end of the support surface 31m, and the front side of the support surface 31m is open without the fall prevention plate 34.

For example, the fall prevention plate 34 is formed by bending a single sheet metal. For example, the fall prevention plate 34 is disposed around the support surface 31m such that the medium M that are significantly smaller than the support surface 31m do not fall from the support surface 31m. The support surface 31m can be lifted and lowered as to described later, and the fall prevention plate 34 is fixed so as not to be lifted and lowered. The fall prevention plate 34 extends over a range from a lowest position to a highest position of the support surface 31m in a height direction. Therefore, it can be said that at least a part of the fall prevention plate 34 is positioned higher than the support surface 31m in a case where the support surface 31m is located at the lowest position.

The height movement mechanism 32 moves the table 31 up and down. When the height movement mechanism 32 moves the table 31 up and down, the support surface 31m can be moved up and down and the medium M supported on the support surface 31m can be lifted and lowered. The height movement mechanism 32 includes a lifting motor 33, a lifting belt 37, and the lifting mechanisms 39. Each of the lifting mechanisms 39 includes a ball screw disposed along the vertical direction, a nut screwed onto the ball screw, and a pulley. The ball screw of the lifting mechanism 39 is rotatably supported by each of the base members 15. The nut of the lifting mechanism 39 is fixed to each of the protruding portions 31n of the table 31. The recording device 1 includes, for example, a set of the lifting mechanisms 39 each including a ball screw, a nut, and a pulley, the lifting mechanisms 39 respectively corresponding to four protruding portions 31n provided at four corners of the table 31. The pulley of the lifting mechanism 39 is fixed to an upper portion of the ball screw. When the pulley of the lifting mechanism 39 rotates, the ball screw rotates, and the protruding portion 31n moves along the vertical direction together with the nut in accordance with the rotation of the ball screw.

The lifting motor 33 is a motor that rotates under the control of the control unit 101. The control unit 101 controls a rotation direction and rotation speed of the lifting motor 33. The lifting belt 37 is an annular belt wound around an output shaft of the lifting motor 33 and the pulleys of four lifting mechanisms 39. The lifting belt 37 is driven to circulate by the rotation of the lifting motor 33. The lifting belt 37 transmits the rotation of the lifting motor 33 to the pulleys of the four lifting mechanisms 39. In this way, the ball screws of the lifting mechanisms 39 rotate to move the table 31 along the vertical direction. Since the four lifting mechanisms 39 are operated in conjunction with each other by the lifting belt 37 to move the table 31, for example, the table 31 can be lifted and lowered while the support surface 31m is kept horizontal.

The rotation direction of the lifting motor 33 can be switched between a forward direction in which the table 31 is moved upward and a reverse direction in which the table 31 is moved downward. The recording device 1 lifts and lowers the table 31 by operating the lifting motor 33.

The driving mechanism 90 includes a pair of the guide shafts 91 and a frame driving unit 60. Each of the guide shafts 91 is a shaft-like member extending over a pair of the base members 15 and disposed along the front-rear direction.

The frame driving unit 60 includes a frame moving motor 61, a transmission belt 63, a speed change mechanism 65, and a transmission belt 67. The frame moving motor 61 is a motor that rotates under the control of the control unit 101. The transmission belt 63 is an annular belt stretched between an output shaft of the frame moving motor 61 and the speed change mechanism 65, and transmits a driving force of the frame moving motor 61 to the speed change mechanism 65. The speed change mechanism 65 includes a first pulley and a second pulley. The transmission belt 63 is wound around the first pulley, and the transmission belt 67 is wound around the second pulley. The speed change mechanism 65 drives the transmission belt 67 by rotating the second pulley with the driving force transmitted from the transmission belt 63 to the first pulley. The speed change mechanism 65 transmits the driving force of the frame moving motor 61 to the transmission belt 67 at a deceleration ratio corresponding to a ratio between the diameter of the first pulley and the diameter of the second pulley.

The transmission belt 67 is an annular belt stretched between the speed change mechanism 65 and a frame moving pulley 17 disposed at an end portion of the base member 15 in a rear direction. The frame moving pulley 17 is a pulley that is installed so as to freely rotate with respect to the base member 15. The transmission belt 67 is disposed along the guide shaft 91.

The movement unit 70 includes a main frame 71, a pair of legs 73, and a carriage 89. The main frame 71 is a plate member that is long in the left-right direction. A pair of the legs 73 are fitted to a pair of the guide shafts 91, and are movable along the guide shafts 91. The main frame 71 is fixed to the top of a pair of the legs 73, and is supported by a pair of the legs 73 from below. The main frame 71 moves together with a pair of the legs 73 in the front-rear direction while being guided by a pair of the guide shafts 91.

Of a pair of the legs 73, a leg 73 supporting the left end of the main frame 71 is fixed to the transmission belt 67 via a belt coupling portion 79. Thus, when the transmission belt 67 is driven to circulate, power for moving the legs 73 in the front-rear direction is applied to the legs 73. In this way, the movement unit 70 moves in the front-rear direction. Note that the lower end of the main frame 71 is positioned higher than the support surface 31m in a case where the table 31 is positioned at an uppermost position. Thus, the main frame 71 moves in the front-rear direction above the support surface 31m, without interfering with the support surface 31m.

The rotation direction of the frame moving motor 61 can be switched between a forward direction in which the main frame 71 moves in the front direction, and a reverse direction in which the main frame 71 moves in the rear direction. The recording device 1 moves the main frame 71 forward and rearward by operating the frame moving motor 61.

The carriage 89 is a substantially cuboid box, and is supported by the main frame 71 via a carriage guide shaft 83. The carriage guide shaft 83 is a shaft-like member fixed to the main frame 71 and extends in the left-right direction along the main frame 71. The carriage guide shaft 83 supports the carriage 89 such that the carriage 89 is movable in the left-right direction. Note that the lower end of the carriage 89 is positioned higher than the support surface 31m in a case where the table 31 is positioned at the uppermost position. Thus, the carriage 89 moves above the support surface 31m in the front-rear direction and the left-right direction, without interfering with the support surface 31m.

Furthermore, the carriage 89 is coupled to a carriage driving belt 85. The carriage driving belt 85 is an annular belt disposed along the carriage guide shaft 83 by having one end wound around a carriage driving pulley 86 and the other end wound around an output shaft of a carriage driving motor 87. The carriage driving pulley 86 is a pulley that is rotatably fixed to the right end of the main frame 71. The carriage driving motor 87 is a motor that is fixed to the left end of the main frame 71 and rotates the output shaft thereof under the control of the control unit 101. The carriage driving motor 87 rotates the output shaft to drive the carriage driving belt 85 to circulate. In this way, the carriage driving motor 87 moves the carriage 89 coupled to the carriage driving belt 85 in the left-right direction along the carriage guide shaft 83.

The driving mechanism 90, the carriage driving belt 85, the carriage driving pulley 86, and the carriage driving motor 87 correspond to an example of a moving mechanism that relatively moves the carriage 89 with respect to the medium M.

The carriage 89 includes the recording head 89a and the irradiation unit 89b. The recording head 89a includes a plurality of nozzles (not illustrated) that open downward from the lower end surface of the carriage 89. The recording head 89a ejects a liquid from these nozzles by driving piezoelectric actuators (not illustrated). When the recording head 89a ejects the liquid from the nozzles, the ejected liquid flies between the nozzles and the medium M placed at the table 31 and lands on the medium M. Note that in the present embodiment, the liquid ejected from the nozzle of the recording head 89a is an ink to be cured by an ultraviolet ray. The recording head 89a records characters and images formed by the liquid on the medium M, by causing the liquid to land on the medium M on the medium support portion 30. The recording head 89a corresponds to an example of a recording unit.

The irradiation unit 89b includes an irradiation window (not illustrated) facing downward from the lower end surface of the carriage 89. The irradiation window is constituted by a plate made of a light-transmissive material. The irradiation unit 89b emits irradiation light from a light-source unit (not illustrated) through the irradiation window. The irradiation light emitted from the irradiation unit 89b passes between the irradiation window and the medium M placed at the table 31, and is emitted onto the medium M on which the recording has been performed by the recording head 89a. In the present embodiment, the irradiation unit 89b is provided with an ultraviolet light emitting diode (UV-LED) that emits ultraviolet rays, and the irradiation light is the ultraviolet ray. In other words, in the present embodiment, the irradiation unit 89b emits the ultraviolet ray to the ink that has landed on the medium M and is cured by the ultraviolet ray, and thus the ink is fixed onto the medium M.

The ink ejected from the recording head 89a is a so-called UV ink which is cured by being irradiated with the ultraviolet ray. Some UV inks have a unique odor. When the recording device 1 performs recording on the medium M by using the ink, the odor of the ink floats inside the housing 10. As the recording head 89a moves in the front-rear direction and the left-right direction at the time of recording, the odor of the ink is diffused inside the housing 10. The first deodorization portion 20 and the second deodorization portion 50 remove an odor emitted from the ink by sucking air inside the housing 10, and discharge cleaned air.

As illustrated in FIG. 2, the first deodorization portion 20 is disposed on the left side of the medium support portion 30. The first deodorization portion 20 is located within a range R1 in which the carriage 89 moves in the left-right direction. In the range R1, a range in which the recording head 89a performs recording on the medium M is referred to as a recording range R2. The recording range R2 is a range in which the recording head 89a faces the support surface 31m in a direction along the X-axis. In the range R1, a range other than the recording range R2 is set as a retraction range. In the retraction range, the recording head 89a does not face the support surface 31m. As illustrated in FIG. 2, the first deodorization portion 20 is disposed such that at least a part of the first deodorization portion 20 is located in the retraction range. The position of the first deodorization portion 20 is close to the position of the recording head 89a when the recording head 89a ejects the ink, and is a position that does not interfere with the ejecting of the ink from the recording head 89a. Therefore, by using the first deodorization portion 20, it is possible to efficiently deodorize the odor of the ink used for recording without affecting the recording operation of the recording device 1.

As illustrated in FIG. 2, the second deodorization portion 50 is disposed on the rear side of the medium support portion 30. The second deodorization portion 50 is positioned between a pair of the guide shafts 91 in a direction along the X-axis, and at least a part of the second deodorization portion 50 overlaps the support surface 31m. The second deodorization portion 50 is positioned behind the table 31 in a direction along the Y-axis. Furthermore, the second deodorization portion 50 is disposed on a side opposite to the front surface cover 11 with the medium support portion 30 interposed therebetween. The position of the second deodorization portion 50 is close to the position of the recording head 89a when the recording head 89a ejects the ink, and is a position that does not interfere with the ejecting of the ink from the recording head 89a. Therefore, by using the second deodorization portion 50, it is possible to efficiently deodorize the odor of the ink used for recording without affecting the recording operation of the recording device 1.

One of the first deodorization portion 20 and the second deodorization portion 50, which are two deodorization portions of the recording device 1, is located at a position aligned with the support surface 31m in the direction along the X-axis, and the other one is located at a position aligned with the support surface 31m in the direction along the Y-axis. The first deodorization portion 20 is located at a position suitable for deodorizing the odor diffused by the movement of the carriage 89 along the X-axis. The second deodorization portion 50 is located at a position suitable for deodorizing the odor diffused by the movement of the carriage 89 along the Y-axis together with the movement unit 70. As described above, the first deodorization portion 20 and the second deodorization portion 50, which are a plurality of deodorization portions, are disposed at a position aligned with the medium support portion 30 in the direction along the X-axis and at a position aligned with the medium support portion 30 in the direction along the Y-axis, and it is possible to efficiently deodorize the air inside the housing 10.

The first deodorization portion 20 and the second deodorization portion 50 are fixed to the base member 15 or the bottom plate 13 by means of a screw.

In the configuration illustrated in FIG. 2, the first deodorization portion 20 and the second deodorization portion 50 are disposed such that at least a part of the medium support portion 30 overlaps a position between the first deodorization portion 20 and the second deodorization portion 50 in plan view. With this configuration, it is possible to more efficiently deodorize the odor of the ink ejected from the recording head 89a to the medium support portion 30.

In the configuration illustrated in FIG. 2, in a configuration in which the medium support portion 30 has the rectangular table 31, the first deodorization portion 20 and the second deodorization portion 50 are disposed so as to correspond to any of four sides constituting the peripheral edge of the table 31.

In other words, the first deodorization portion 20 and the second deodorization portion 50 are disposed so as to face any one of four sides constituting the peripheral edge of the table 31. In this configuration, the first deodorization portion 20 and the second deodorization portion 50 are disposed such that the side of the table 31 facing the first deodorization portion 20 and the side of the table 31 facing the second deodorization portion 50 do not face each other.

Furthermore, in the configuration illustrated in FIG. 2, the first deodorization portion 20 and the second deodorization portion 50 are disposed so as not to face each other with the medium support portion 30 interposed therebetween.

2. Configuration of Deodorization Portion

Figure 5:
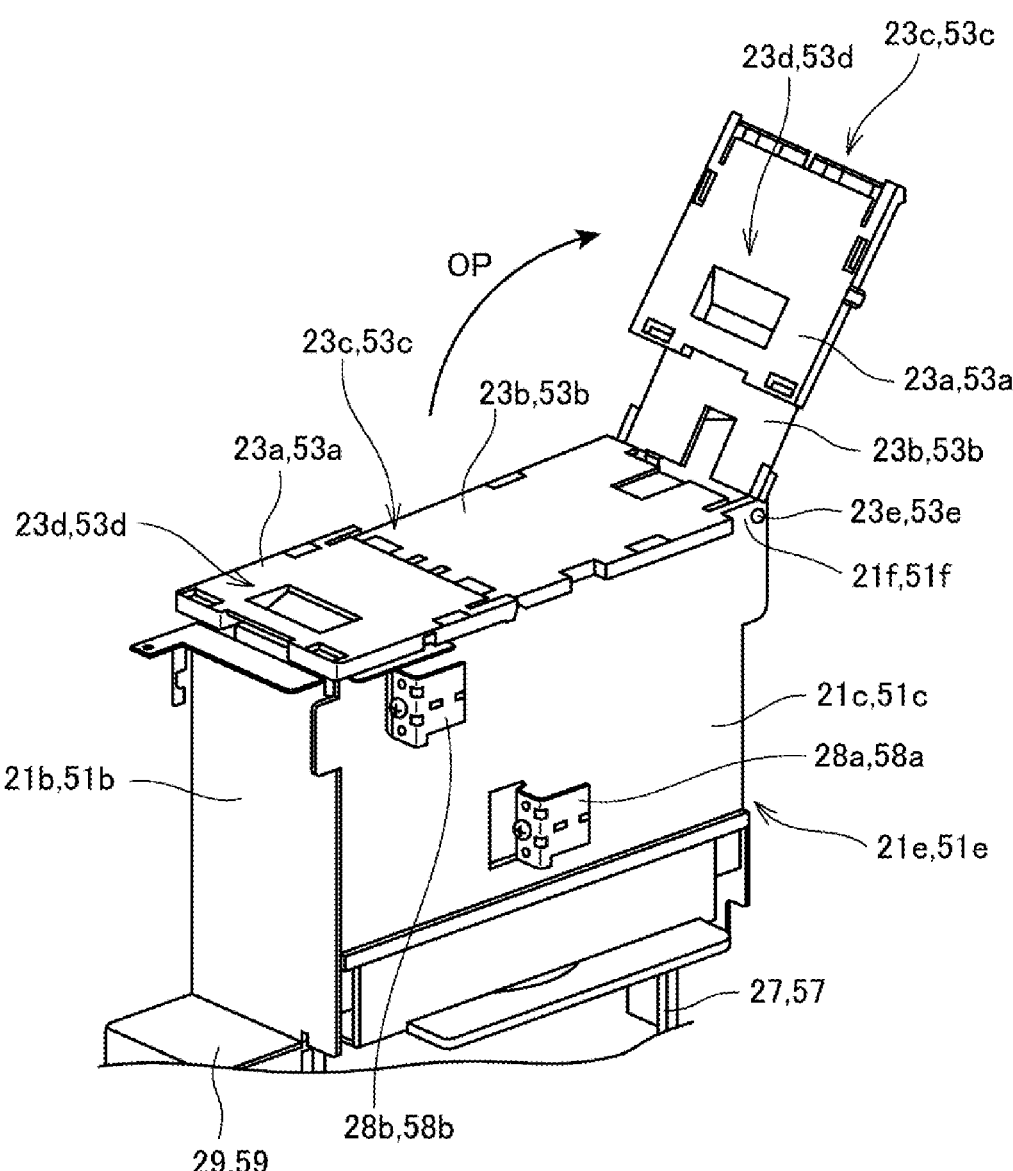
FIG. 5 is a perspective view of a deodorization portion.

FIGS. 4 and 5 are perspective views of the deodorization portion. FIG. 4 is a front perspective view of the deodorization portion, and FIG. 5 is a rear perspective view of the deodorization portion.

The first deodorization portion 20 and the second deodorization portion 50 have a common configuration. Hereinafter, the configuration of the first deodorization portion 20 will be described, but the description is also applied to the second deodorization portion 50.

The up-down direction in FIGS. 4 and 5 corresponds to the up-down direction in a case where the first deodorization portion 20 and the second deodorization portion 50 are installed in the recording device 1.

The first deodorization portion 20 has a substantially box-like accommodation portion 21. A front surface 21a, a side surface 21b, a side surface 21d, a back surface 21c, and a bottom surface 21e, which constitute the accommodation portion 21, are made of a surface material formed of an incombustible or flame-retardant material. For example, the accommodation portion 21 is made by a metal plate such as a steel plate. The upper surface of the accommodation portion 21 is open, and a lid portion 23 is disposed so as to cover the opening.

The front surface 21a is a surface facing the back surface 21c, and the side surface 21b is a surface facing the side surface 21d. A lid support portion 21f is provided at the upper end of the side surface 21b and the upper end of the side surface 21d. The lid support portion 21f protrudes toward the outside of the accommodation portion 21 at the side surface 21b and the side surface 21d. The lid support portion 21f on the side surface 21b side and the lid support portion 21f on the side surface 21d side face each other.

The lid portion 23 has a distal end panel 23a and a proximal end panel 23b, and has a configuration in which the distal end panel 23a and the proximal end panel 23b are coupled by a hinge portion 23c. A proximal end portion of the proximal end panel 23b is rotatably coupled to the lid support portion 21f of the side surface 21b and the lid support portion 21f of the side surface 21d via a support portion 23e. The distal end portion of the proximal end panel 23*b* is rotatably coupled to the proximal end portion of the distal end panel 23*a* by the hinge portion 23*c*. Therefore, the distal end panel 23*a* and the proximal end panel 23*b* are rotatable with respect to each other, and the proximal end panel 23*b* is rotatable with respect to the accommodation portion 21. For example, the distal end panel 23*a* and the proximal end panel 23*b* are made of synthetic resins. Furthermore, similarly to the front surface 21*a*, the side surface 21*b*, the side surface 21*d*, the back surface 21*c*, and the bottom surface 21*e*, the distal end panel 23*a* and the proximal end panel 23*b* may be made of a surface material formed of an incombustible or flame-retardant material.

A recess 23*d* is formed on the distal end panel 23*a*. The recess 23*d* is used for a user to hook his/her finger when the user opens the lid portion 23.

A first intake port 25 is open in an upper portion of the accommodation portion 21. The first intake port 25 is an opening formed by cutting out a part of the upper portion of the front surface 21*a*. In the present embodiment, the first intake port 25 is formed only on the front surface 21*a* and is not formed on the back surface 21*c*. The front surface 21*a* is a surface facing the medium support portion 30 in a state in which the first deodorization portion 20 is installed in the recording device 1. It is also possible to adopt a configuration in which the first intake port 25 is provided on a surface other than the front surface 21*a* in the accommodation portion 21. However, by providing the first intake port 25 only on the front surface 21*a*, the air flow in the first deodorization portion 20 is limited in a specific direction, and the deodorization by the first deodorization portion 20 can be performed more efficiently.

A deodorization unit 40 is accommodated in the accommodation portion 21. Since the first intake port 25 is open on the side surface 21*b*, the upper surface of the deodorization unit 40 is exposed to the inside of the housing 10. The deodorization unit 40 is removably accommodated in the accommodation portion 21, and the deodorization unit 40 can be replaced. On the other hand, a first air blower 27 is attached to a lower portion of the accommodation portion 21. The first air blower 27 includes a fan (not illustrated) and a casing surrounding the fan. The fan of the first air blower 27 faces the inside of the accommodation portion 21 through an opening (not illustrated) formed on the bottom surface 21*e*. An opening is provided in a casing of the first air blower 27, and a duct 29 is coupled to the first air blower 27 so as to cover the opening.

The first air blower 27 sucks air inside the accommodation portion 21 and discharges the air to the duct 29. The duct 29 guides the discharged air from the first air blower 27 to the lower side of the first deodorization portion 20. By the operation of the first air blower 27, the air inside the housing 10 is sucked from the first intake port 25. This air passes through the inside of the accommodation portion 21, passes through the first air blower 27 and the duct 29, and is discharged from the lower side of the first deodorization portion 20.

As described above, the first deodorization portion 20 and the second deodorization portion 50 have a common configuration. For example, the second deodorization portion 50 includes an accommodation portion 51 corresponding to the accommodation portion 21, a lid portion 53 corresponding to the lid portion 23, a second air blower 57 corresponding to the first air blower 27, and a duct 59 corresponding to the duct 29. Similarly to the accommodation portion 21, the accommodation portion 51 has a front surface 51*a*, a side surface 51*b*, a side surface 51*d*, a back surface 51*c*, and a bottom surface 51*e*, and a second intake port 55 is open on the front surface 51*a* of the upper portion of the accommodation portion 51. Similarly to the lid portion 23, the lid portion 53 includes a distal end panel 53*a*, a proximal end panel 53*b*, a hinge portion 53*c*, a recess 53*d*, and a support portion 53*e*. As illustrated in FIGS. 4 and 5, these components correspond to the components of the first deodorization portion 20.

The deodorization unit 40 is accommodated in the accommodation portion 51. The deodorization unit 40 is removably accommodated in the accommodation portion 51, and the deodorization unit 40 can be replaced. As the deodorization unit 40 accommodated in the accommodation portion 51 and the deodorization unit 40 accommodated in the accommodation portion 21, a common unit can be used. That is, the deodorization unit 40 can be attached to both the first deodorization portion 20 and the second deodorization portion 50.

3. Configuration of Deodorization Unit

Figure 6:
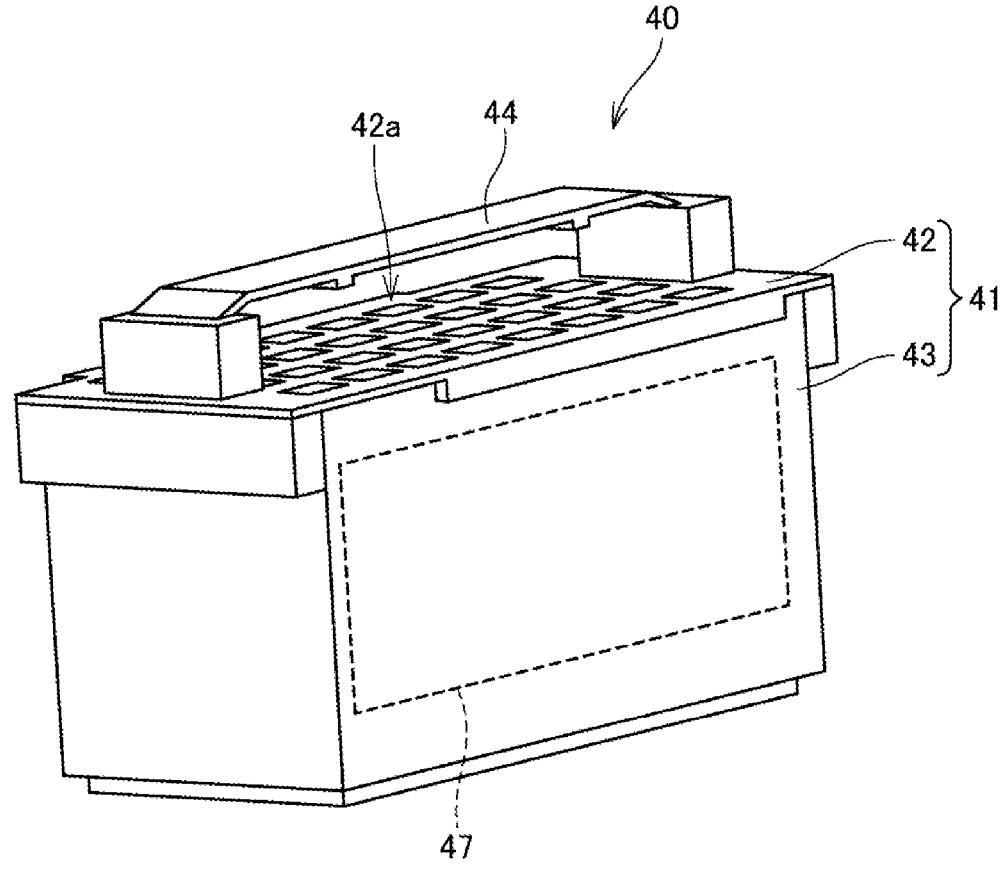
FIG. 6 is a perspective view of a deodorization unit.
Figure 7:
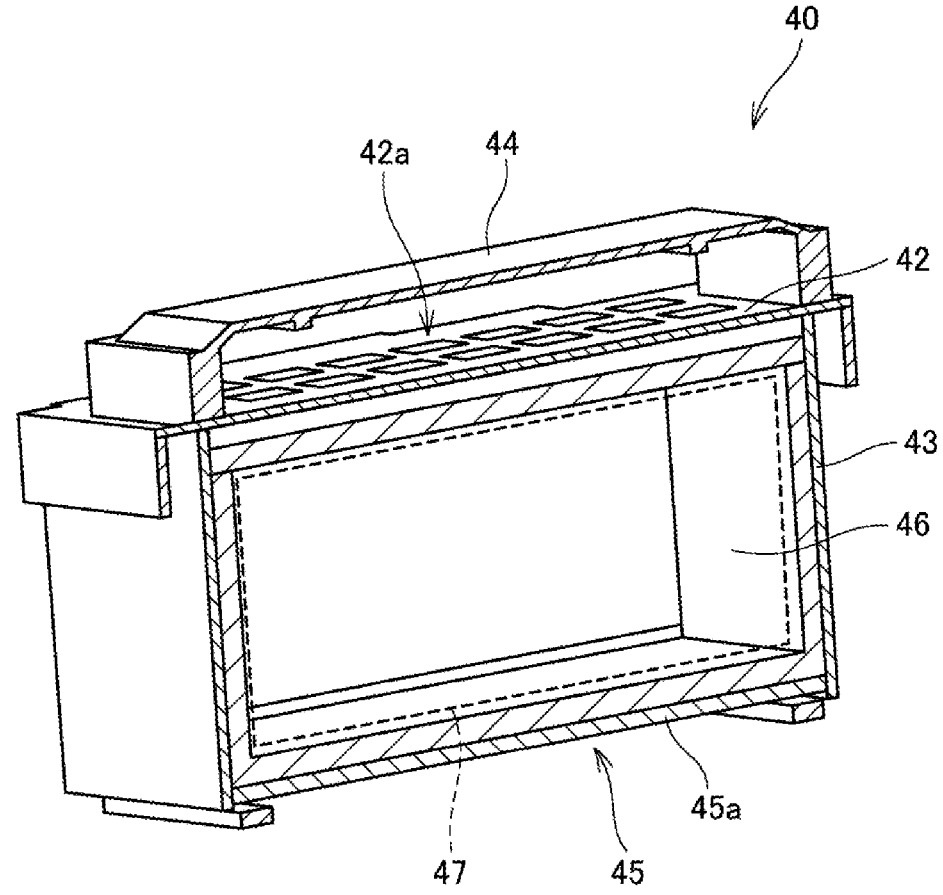
FIG. 7 is a cross-sectional view of a main part of a deodorization unit.

FIG. 6 is a perspective view of the deodorization unit 40, and FIG. 7 is a cross-sectional view of a main part of the deodorization unit 40.

The deodorization unit 40 has a deodorization body cover 41. The deodorization body cover 41 has an upper cover 42 constituting the upper surface of the deodorization body cover 41 and a cover body 43. The cover body 43 is a substantially box-like container, and as illustrated in FIG. 7, a support member 46 is disposed on the inner surface of the cover body 43. The cover body 43 accommodates a deodorization body 47.

The deodorization body 47 is an adsorbent adsorbing a substance emitting an odor or a decomposing agent for decomposing a substance emitting an odor. Examples of the adsorbent include activated carbon and zeolite. Examples of the decomposing agent include a catalyst using platinum or the like supported on a carrier made of ceramics or the like. The support member 46 holds the deodorization body 47 such that the deodorization body 47 does not move inside the cover body 43. The support member 46 may be made of an elastic material. In this case, the support member 46 has a function of protecting the deodorization body 47 from impact.

An opening (not illustrated) is formed on the bottom surface of the cover body 43. Upper surface vent holes 42*a* are open on the upper cover 42. These openings allow air to flow between the space inside the cover body 43 and the outside thereof.

A handle 44 is attached to the upper cover 42. By holding the handle 44, the user can lift the deodorization unit 40 without touching the deodorization body 47.

In a state in which the deodorization unit 40 is accommodated in the first deodorization portion 20, the air flowing into the accommodation portion 21 from the first intake port 25 is sent to the deodorization body 47 through the upper surface vent holes 42*a* by the operation of the first air blower 27. After this air passes through the deodorization body 47, the air is discharged from the opening provided on the bottom surface of the cover body 43 and flows to the first air blower 27 through the bottom surface 21*e*.

The front surface 21*a*, the side surface 21*b*, the back surface 21*c*, the side surface 21*d*, and the bottom surface 21*e*, which constitute the accommodation portion 21, are made of an incombustible or flame-retardant material. Similarly, the front surface 51*a*, the side surface 51*b*, the back surface 51*c*, the side surface 51*d*, and the bottom surface 51*e*, which constitute the accommodation portion 51, are made of an incombustible or flame-retardant material. In a case where a combustible material such as activated carbon is used as the deodorization body 47, it is necessary to consider the risk of ignition of the deodorization body 47. In the recording device 1, since five surfaces of the accommodation portion 21 and the accommodation portion 51 are formed of an incombustible or flame-retardant material, it is possible to minimize the risk when the deodorization body 47 is ignited. Thus, a combustible material can be used as the deodorization body 47. Therefore, the degree of freedom of selection of the deodorization body 47 is high, and efficient deodorization can be achieved by using the deodorization body 47 suitable for the ink which is an odor source.

4. Replacement of the Deodorization Unit

In the first deodorization portion 20 and the second deodorization portion 50, the deodorization unit 40 is replaceable. That is, the user can take out the deodorization unit 40 attached to the first deodorization portion 20 and set a new deodorization unit 40 in the first deodorization portion 20. When the operation of replacing the deodorization unit 40 is performed, the user can easily use the deodorization unit 40 by holding the handle 44.

As illustrated in FIG. 5, when the user hooks his/her finger on the recess 23d and lifts the distal end panel 23a, the lid portion 23 rotates about the support portion 23e in an OP direction of FIG. 5. Thus, the lid portion 23 is lifted and the upper surface of the accommodation portion 21 is opened. In a state in which the lid portion 23 is opened, by rotating the distal end panel 23a about the hinge portion 23c, the lid portion 23 can be folded such that the distal end panel 23a and the proximal end panel 23b overlap with each other as illustrated in FIG. 5. Note that FIG. 5 illustrates the lid portion 23 in both a state in which the lid portion 23 is closed and a state in which the lid portion 23 is opened.

Since the upper portion of the accommodation portion 21 is opened in a state in which the lid portion 23 is opened, the user can perform an operation of taking out the deodorization unit 40 from the accommodation portion 21 and an operation of inserting the deodorization unit 40 into the accommodation portion 21. Thus, in the first deodorization portion 20 and the second deodorization portion 50, the deodorization unit 40 can be easily replaced. In the operation of replacing the deodorization unit 40, the user can take out and attach the deodorization unit 40 by holding the handle 44 with a hand. Thus, replacement of the deodorization unit 40 can be performed with a simple operation.

As illustrated in FIG. 5, a first deodorization body sensor 28a and a first lid sensor 28b are disposed on the back surface 21c of the first deodorization portion 20. The first deodorization body sensor 28a is a sensor that detects whether or not the deodorization unit 40 is accommodated in the accommodation portion 21. The first lid sensor 28b is a sensor that detects whether or not the lid portion 23 is closed. The first deodorization body sensor 28a and the first lid sensor 28b are constituted by, for example, a switch-type sensor, a reflective optical sensor, or the like.

Similarly, a second deodorization body sensor 58a and a second lid sensor 58b are disposed on the back surface 51c of the second deodorization portion 50. The second deodorization body sensor 58a is a sensor that detects whether or not the deodorization unit 40 is accommodated in the accommodation portion 51. The second lid sensor 58b is a sensor that detects whether or not the lid portion 53 is closed. The second deodorization body sensor 58a and the second lid sensor 58b are constituted by, for example, a switch-type sensor, a reflective optical sensor, or the like.

The first deodorization body sensor 28a and the first lid sensor 28b are coupled to the control unit 101. The control unit 101 can detect whether or not the deodorization unit 40 is attached to the first deodorization portion 20 based on the detection value of the first deodorization body sensor 28a. Furthermore, the control unit 101 detects whether or not the lid portion 23 is closed based on the detection value of the first lid sensor 28b.

The second deodorization body sensor 58a and the second lid sensor 58b are coupled to the control unit 101. The control unit 101 can detect whether or not the deodorization unit 40 is attached to the second deodorization portion 50 based on the detection value of the second deodorization body sensor 58a. Furthermore, the control unit 101 detects whether or not the lid portion 53 is closed based on the detection value of the second lid sensor 58b.

The first deodorization body sensor 28a and the second deodorization body sensor 58a correspond to an example of the deodorization body sensor, and the first lid sensor 28b and the second lid sensor 58b correspond to an example of the lid portion sensor.

As illustrated in FIGS. 1 and 3, a side surface cover 14 is provided on a left side surface 10d of the housing 10 so as to correspond to a position at which the first deodorization portion 20 is provided. The side surface cover 14 is rotatably coupled to the left side surface 10d by an upper end hinge thereof. Therefore, the side surface cover 14 can be opened upward from below. Furthermore, the side surface cover 14 may 14 may have a configuration in which the lower end of the side surface cover 14 is rotatably coupled to the bottom plate 13 such that the side surface cover 14 can be opened by being rotated downward. The side surface cover 14 corresponds to an example of a first cover, the left side surface 10d constituted by the side surface cover 14 corresponds to an example of a first surface, and an opening formed by opening the side surface cover 14 corresponds to an example of a first opening. The front surface cover 11 corresponds to an example of a second cover, the front surface 10a constituted by the front surface cover 11 corresponds to an example of a second surface, and an opening formed by opening the front surface cover 11 corresponds to an example of a second opening.

By opening the side surface cover 14, the first deodorization portion 20 is exposed to the left side surface 10d. The user can replace the deodorization unit 40 by opening the lid portion 23 in a state in which the side surface cover 14 is opened.

On the other hand, the second deodorization portion 50 is positioned behind the medium support portion 30. As illustrated in FIG. 3, in a state in which the front surface cover 11 is opened, the second deodorization portion 50 is exposed to the inner side of the housing 10. The user can open the front surface cover 11, open the lid portion 23 by inserting his/her hand into the back of the housing 10, and replace the deodorization unit 40 of the second deodorization portion 50.

As illustrated in FIGS. 1 and 3, a front surface cover sensor 11c is attached to the front surface 10a of the housing 10. The front surface cover sensor 11c is a sensor that detects whether or not the front surface cover 11 is closed. Furthermore, a side surface cover sensor 14c is attached to the left side surface 10d. The side surface cover sensor 14c is a sensor that detects whether or not the side surface cover 14 is closed. The front surface cover sensor 11c and the side surface cover sensor 14c are constituted by, for example, a switch-type sensor, a reflective optical sensor, or the like. The front surface cover sensor 11c and the side surface cover sensor 14c are coupled to the control unit 101. The control unit 101 detects whether or not the front surface cover 11 is closed based on the detection value of the front surface cover sensor 11c. Furthermore, the control unit 101 detects whether or not the side surface cover 14 is closed based on the detection value of the side surface cover sensor 14c. The side surface cover sensor 14c corresponds to an example of a first sensor, and the front surface cover sensor 11c corresponds to an example of a second sensor.

As described above, the first deodorization portion 20 is positioned outside the recording range R2 in the range R1 in which the carriage 89 moves in the left-right direction. Accordingly, the carriage 89 may move to a position overlapping the first deodorization portion 20. Thus, the first deodorization portion 20 is disposed such that the upper end of the first deodorization portion 20 is positioned lower than the lower end of the carriage 89. Therefore, it is possible to install the first deodorization portion 20 in the range R1 without disturbing the recording operation of the recording device 1, and it is possible to reduce the size of the recording device 1.

The first deodorization portion 20 is disposed such that the first intake port 25 faces the table 31. That is, in the first deodorization portion 20, the first intake port 25 is open to the front surface 21a facing the table 31. Thus, the air containing the odor of the ink ejected from the recording head 89a to the medium M placed at the table 31 can be efficiently taken in from the first intake port 25.

In this configuration, when air is sucked from the first intake port 25 by the power of the first air blower 27, an air flow from the support surface 31m toward the first intake port 25 is generated. When the first intake port 25 is located at a position higher than the support surface 31m, the air flow from the support surface 31m toward the first intake port 25 becomes strong. Therefore, the motion of the ink ejected by the recording head 89a and the state of the ink on the surface of the recording head 89a may be affected. Therefore, it is preferable that the first intake port 25 is installed such that the upper end of the first intake port 25 is located at a position lower than the support surface 31m of the table 31 in the height direction. That is, it is preferable that the first intake port 25 is located at a position not overlapping the support surface 31m in the height direction.

Furthermore, the second deodorization portion 50 is positioned within or outside the range in which the movement unit 70 moves in the front-rear direction. Thus, the second deodorization portion 50 is disposed such that the upper end of the second deodorization portion 50 is positioned lower than the lower end of the main frame 71. Therefore, the second deodorization portion 50 can be installed in a range in which the main frame 71 moves.

The second deodorization portion 50 is disposed behind the table 31 such that the second intake port 55 faces the table 31. That is, in the second deodorization portion 50, the second intake port 55 is open to the front surface 51a facing the table 31. Thus, the air containing the odor of the ink ejected from the recording head 89a to the medium M placed at the table 31 can be efficiently taken in from the second intake port 55.

Furthermore, the second deodorization portion 50 is disposed such that at least a part of the second intake port 55 overlaps the support surface 31m in the height direction in a state in which the table 31 is positioned at the uppermost portion. In other words, at least a part of the second intake port 55 is located at a position higher than the table 31. With this configuration, it is possible to efficiently take in the air containing the odor of the ink ejected onto the medium M from the second intake port 55.

As described above, the first deodorization portion 20 is positioned within the range R1 and close to the table 31. On the other hand, the second deodorization portion 50 is positioned behind the table 31. The distance from the left end of the table 31 to the first intake port 25 in the direction along the X-axis is shorter than the distance from the rear end of the table 31 to the second intake port 55 in the direction along the Y-axis. In other words, the second deodorization portion 50 is farther away from the table 31 than the first deodorization portion 20. Thus, the influence of the air flow from the support surface 31m toward the second intake port 55 on the ink is small. Therefore, it is preferable that the second intake port 55 is located at a position overlapping the support surface 31m in the height direction when the support surface 31m is positioned at the uppermost portion.

The first intake port 25 and the second intake port 55 are open at different positions in the height direction. Therefore, the first deodorization portion 20 and the second deodorization portion 50 take in the air at different positions, and thus the odor diffused inside the housing 10 can be more efficiently deodorized.

Furthermore, in the recording device 1, the first deodorization portion 20 faces the medium support portion 30 in the direction along the X-axis, and the second deodorization portion 50 faces the medium support portion 30 in one direction along the Y-axis. Therefore, it is possible to more efficiently deodorize the odor diffused inside the housing 10 by the movement of the carriage 89 with respect to the medium M.

5. Configuration of Control System of Recording Device

Figure 8:
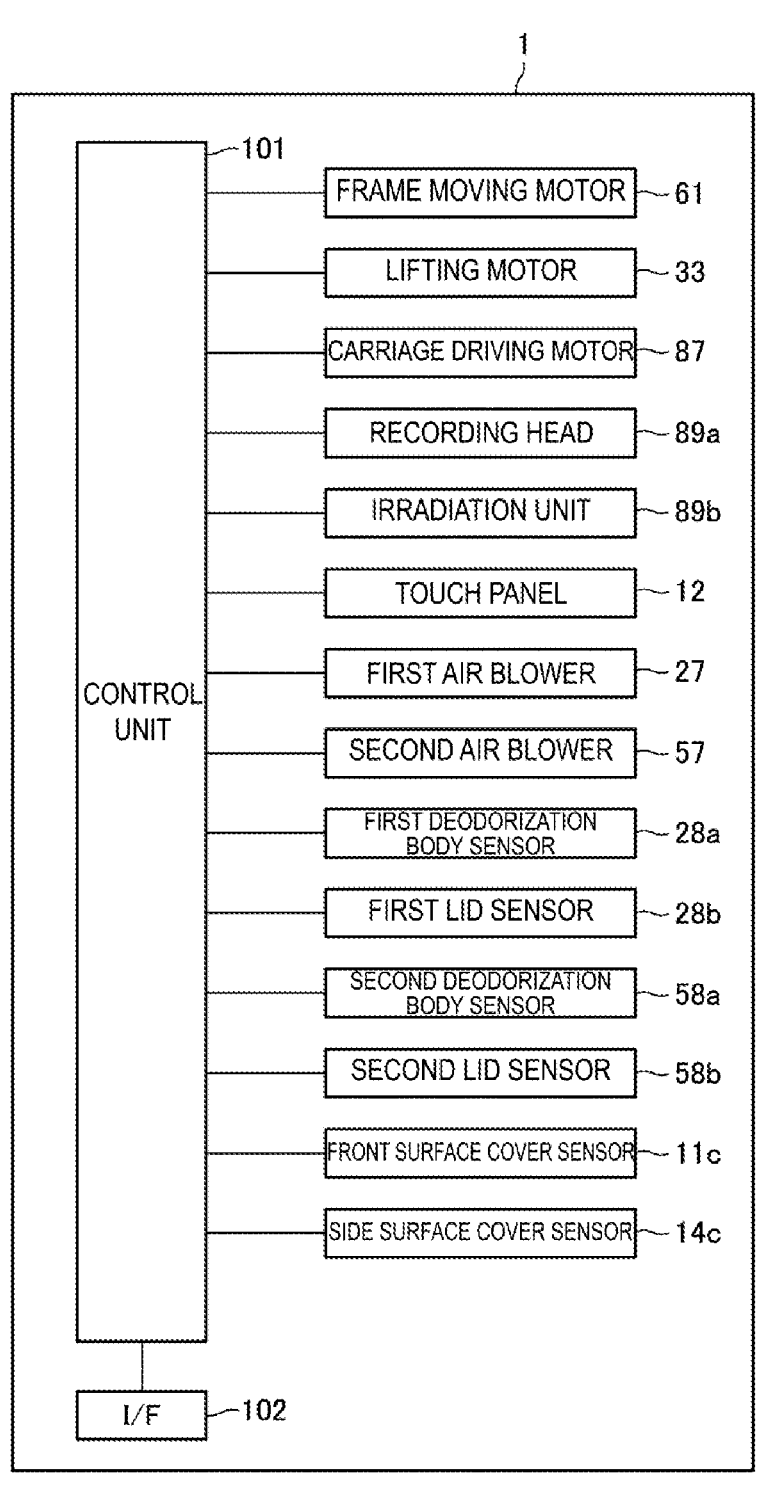
FIG. 8 is a block diagram illustrating a configuration of a control system of a recording device.

FIG. 8 is a block diagram illustrating a functional configuration of a control system of the recording device 1.

The recording device 1 includes a control unit 101. The control unit 101 is a computer including a processor such as a central processing unit (CPU) or a micro processing unit (MPU), and a storage unit. The storage unit of the control unit 101 includes a volatile memory and a nonvolatile storage unit. The volatile memory is, for example, a random access memory (RAM). The nonvolatile storage unit is configured by a read only memory (ROM), a hard disk, a flash memory, or the like. The control unit 101 controls each unit of the recording device 1 by executing a program stored in the storage unit.

An interface (I/F) 102 is coupled to the control unit 101. The interface 102 is a communication device that performs wired communication using a cable or wireless communication using a wireless communication line. The interface 102 communicates with a host computer (not illustrated) to receive recording data. The recording data includes data of images and characters to be recorded on the medium M by the recording device 1, a command for instructing the recording device 1 to executing recording, and other pieces of data.

The frame moving motor 61, the lifting motor 33, the carriage driving motor 87, the recording head 89a, and the irradiation unit 89b are coupled to the control unit 101 as a drive unit related to the recording operation. The control unit 101 performs recording on the medium M by controlling these drive units.

That is, the control unit 101 operates each motor based on the recording data received by the interface 102. Specifically, the control unit 101 moves the movement unit 70 in the front-rear direction by controlling switching of the rotation direction of the frame moving motor 61 and controlling the start and stop of the rotation of the frame moving motor 61. The control unit 101 moves the table 31 in the up-down direction by controlling switching of the rotation direction of the lifting motor 33 and controlling the start and stop of the rotation of the lifting motor 33. The control unit 101 moves the carriage 89 in the left-right direction by controlling switching of the carriage driving motor 87 and controlling the start and stop of the rotation of the carriage driving motor 87.

The control unit 101 operates the recording head 89*a* based on the recording data received by the interface 102 to eject a liquid. The control unit 101 operates the touch panel 12 to display information regarding the recording on the touch panel 12.

For example, in a case where the recording device 1 performs recording on the medium M, the control unit 101 first drives the lifting motor 33 to optimize the gap between the support surface 31*m* and the recording head 89*a*. Next, the control unit 101 drives the frame moving motor 61 and the carriage driving motor 87 to move the main frame 71 from the front side to the rear side and the carriage 89 from the left side to the right side. At the same time, the control unit 101 performs recording by ejecting a liquid from the recording head 89*a* to the medium M based on the recording data. Furthermore, the control unit 101 causes the irradiation unit 89*b* to emit the irradiation light to the medium M on which the recording has been performed, and fixes the liquid on the medium M to the medium M.

After the recording on the medium M is completed, the lifting motor 33 is driven to move the support surface 31*m* to the lowest position.

The touch panel 12 is coupled to the control unit 101. The touch panel 12 functions as an input device that detects a touch operation and a display device that displays information. For example, when the recording is performed on the medium M, the control unit 101 displays information regarding the recording on the touch panel 12. The touch panel 12 corresponds to an example of a notification unit.

The first air blower 27, the second air blower 57, the first deodorization body sensor 28*a*, the first lid sensor 28*b*, the second deodorization body sensor 58*a*, the second lid sensor 58*b*, the front surface cover sensor 11*c*, and the side surface cover sensor 14*c* are coupled to the control unit 101. These are functional units related to deodorization.

The control unit 101 operates the first air blower 27 to perform deodorization by the first deodorization portion 20. Furthermore, the control unit 101 operates the second air blower 57 to perform deodorization by the second deodorization portion 50.

When the recording on the medium M is started, the control unit 101 performs deodorization by operating the first air blower 27 and the second air blower 57 at least either during execution of the recording on the medium M or for a predetermined time after completion of the recording on the medium M.

For example, when the recording on the medium M is started, the control unit 101 starts operations of the first air blower 27 and the second air blower 57, and continues the operations of the first air blower 27 and the second air blower 57 during the execution of recording. As a result, the control unit 101 deodorizes the odor of the ink ejected from the recording head 89*a* for recording.

Furthermore, for example, the control unit 101 operates the first air blower 27 and the second air blower 57 for a predetermined time after the recording on the medium M is ended. During the recording on the medium M, the odor diffuses inside the housing 10 due to the movement of the main frame 71 along the Y-axis direction and the movement of the carriage 89 along the X-axis direction. By operating the first deodorization portion 20 and the second deodorization portion 50 for a predetermined time after the end of recording, the odor diffused inside the housing 10 can be deodorized. Therefore, for example, it is possible to reduce the odor until the user opens the front surface cover 11 in order to take out the medium M on which the recording is completed.

The control unit 101 may not operate the first air blower 27 and the second air blower 57 during the recording on the medium M, and may start the operations of the first air blower 27 and the second air blower 57 after the recording is completed. For example, the control unit 101 operates the first air blower 27 and the second air blower 57 after the carriage 89 returns to a home position which is a position at which flushing or cleaning of the recording head 89*a* is performed or after the support surface 31*m* is moved to the lowest position. In this case, since the first air blower 27 and the second air blower 57 are not operated while the ink is ejected from the recording head 89*a*, it is possible to suppress the influence of the air flow generated by the first air blower 27 and the second air blower 57 on the ink.

In a case where the user performs an instruction to replace the deodorization unit 40, the control unit 101 performs control for enabling replacement of the deodorization unit 40 based on the instruction. The instruction by the user is performed using, for example, the touch panel 12. The control unit 101 causes the touch panel 12 to display an operation screen. In a case where a touch operation on the operation screen is detected by the touch panel 12, the control unit 101 receives the operation as an instruction from the user.

The control unit 101 detect whether or not the deodorization unit 40 is attached to the first deodorization portion 20 based on the detection value of the first deodorization body sensor 28*a*. Furthermore, the control unit 101 detects whether or not the lid portion 23 is closed based on the detection value of the first lid sensor 28*b*. In a normal state of the recording device 1, the deodorization unit 40 is attached to the first deodorization portion 20 and the lid portion 23 is closed. The normal state of the recording device 1 refers to a state in which the recording device 1 can perform recording on the medium M. In a case where the control unit 101 determines that the deodorization unit 40 is not attached to the first deodorization portion 20 and determines that the lid portion 23 is not closed, the recording device 1 is not in the normal state and cannot perform recording on the medium M. Therefore, in a case where it is determined that the deodorization unit 40 is not attached to the first deodorization portion 20 and in a case where it is determined that the lid portion 23 is not closed, the control unit 101 detects a deodorization portion error related to the first deodorization portion 20. While the deodorization portion error is detected, the control unit 101 does not start recording on the medium M. In a case where the deodorization portion error is detected, the control unit 101 notifies the user through the touch panel 12. For example, the control unit 101 causes the touch panel 12 to display a message or an image notifying that the deodorization unit 40 is not attached to the first deodorization portion 20 or that the lid portion 23 is not closed. Here, the control unit 101 may cause the touch panel 12 to display a message or an image for requesting confirmation of the first deodorization portion 20. While the deodorization portion error is detected, the control unit 101 may notify the host computer (not illustrated) coupled to the interface 102 of the error.

The control unit 101 determines whether or not the deodorization unit 40 is attached to the second deodorization portion 50 based on the detection value of the second deodorization body sensor 58a. Furthermore, the control unit 101 determines whether or not the lid portion 53 is closed based on the detection value of the second lid sensor 58b. In the normal state of the recording device 1, the deodorization unit 40 is attached to the second deodorization portion 50 and the lid portion 53 is closed. The normal state of the recording device 1 refers to a state in which the recording device 1 can perform recording on the medium M. In a case where the control unit 101 determines that the deodorization unit 40 is not attached to the second deodorization portion 50 and determines that the lid portion 53 is not closed, the recording device 1 is not in the normal state. Therefore, in a case where it is determined that the deodorization unit 40 is not attached to the second deodorization portion 50 and in a case where it is determined that the lid portion 53 is not closed, the control unit 101 detects a deodorization portion error related to the second deodorization portion 50. In this case, the control unit 101 notifies the user through the touch panel 12 as in a case where the deodorization portion error related to the first deodorization portion 20 is detected. For example, the control unit 101 causes the touch panel 12 to display a message or an image notifying that the deodorization unit 40 is not attached to the second deodorization portion 50 or that the lid portion 53 is not closed. Here, the control unit 101 may cause the touch panel 12 to display a message or an image for requesting confirmation of the second deodorization portion 50.

The control unit 101 determines whether or not the front surface cover 11 is closed based on the detection value of the front surface cover sensor 11c. Furthermore, the control unit 101 determines whether or not the side surface cover 14 is closed based on the detection value of the side surface cover sensor 14c. In the normal state of the recording device 1, the front surface cover 11 and the side surface cover 14 are closed. In a case where at least one of the front surface cover 11 and the side surface cover 14 is not closed, the control unit 101 detects a cover error. While the cover error is detected, the control unit 101 does not start recording on the medium M. Furthermore, in a case where the cover error is detected during recording on the medium M, the control unit 101 interrupts the recording on the medium M. In a case where the cover error is detected, the control unit 101 notifies the user through the touch panel 12. For example, the control unit 101 causes the touch panel 12 to display a message or an image notifying that the front surface cover 11 is not closed or that the side surface cover 14 is not closed. Here, the control unit 101 may cause the touch panel 12 to display a message or an image for requesting confirmation of the front surface cover 11 or the side surface cover 14. Furthermore, while the cover error is detected, the control unit 101 may notify the host computer (not illustrated) coupled to the interface 102 of the error.

The control unit 101 does not detect a cover error caused by the front surface cover 11 not being closed while the user installs the medium M at the medium support portion 30 and takes out the medium M from the medium support portion 30. For example, in a case where the user operates the touch panel 12 to instruct installation of the medium M or removal of the medium M, the control unit 101 receives the instruction and transitions to a state in which a cover error related to the front surface cover 11 is not detected. In a case where the user operates the touch panel 12 to perform input that the installation of the medium M or the removal of the medium M is completed, the control unit 101 returns to the original state and enters a state in which the cover error of the front surface cover 11 can be detected.

Furthermore, while the user replaces the deodorization unit 40 of the first deodorization portion 20, the control unit 101 does not detect a cover error caused by the side surface cover 14 not being closed, a deodorization portion error based on the detection value of the first deodorization body sensor 28a, and a deodorization portion error based on the detection value of the first lid sensor 28b. Furthermore, while the user replaces the deodorization unit 40 of the second deodorization portion 50, the control unit 101 does not detect a cover error caused by the front surface cover 11 not being closed, a deodorization portion error based on the detection value of the second deodorization body sensor 58a, and a deodorization portion error based on the detection value of the second lid sensor 58b.

6. Operation of Recording Device

Figure 9:
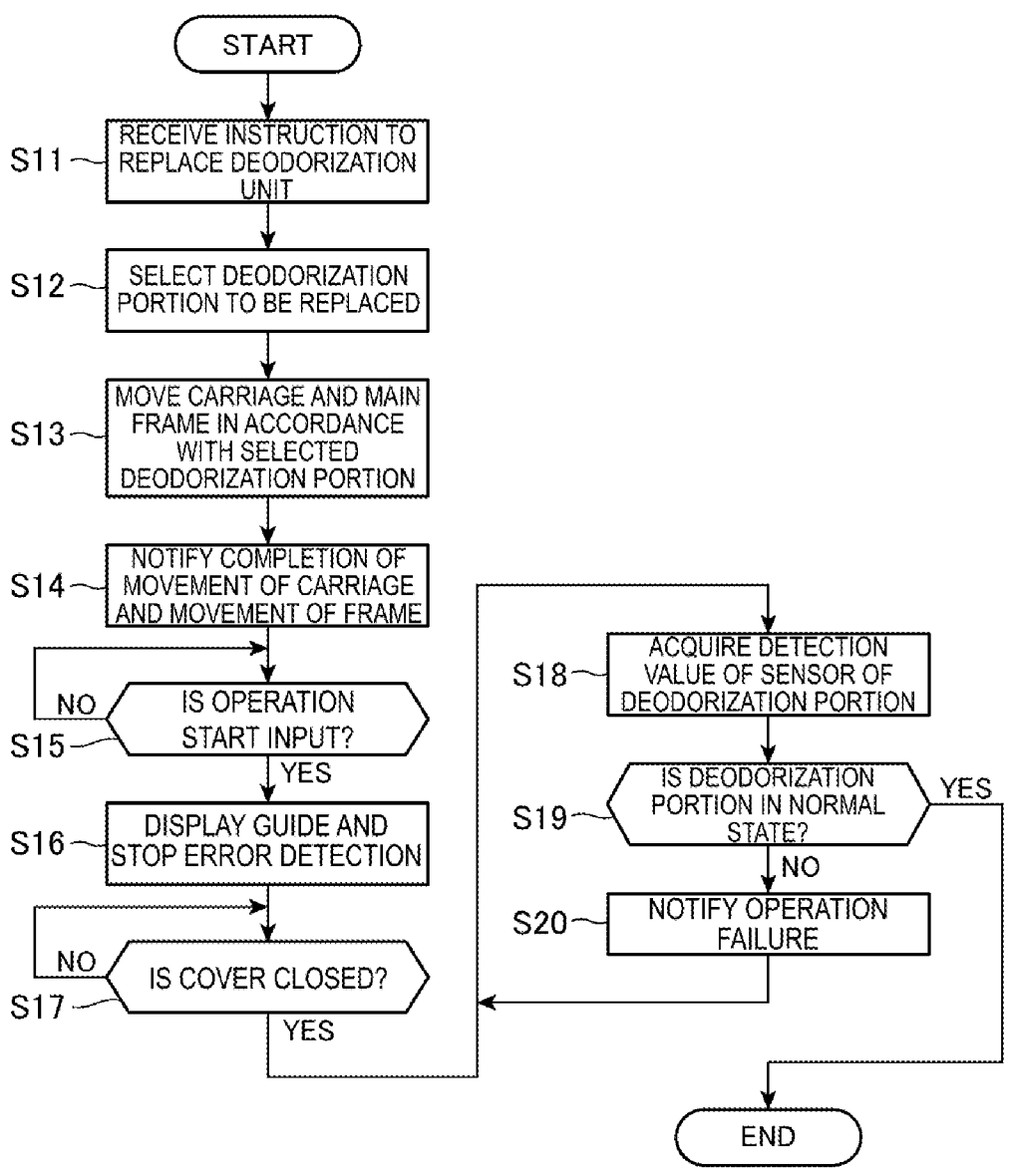
FIG. 9 is a flowchart illustrating an operation of a recording device.

FIG. 9 is a flowchart illustrating the operation of the recording device 1, and illustrates the operation of the recording device 1 in a case where the deodorization unit 40 is replaced in either the first deodorization portion 20 or the second deodorization portion 50. Steps S11 to S20 are executed by the control unit 101.

In a case where the user inputs an instruction to replace the deodorization unit 40 by operating the touch panel 12, the recording device 1 receives the instruction (step S11). Based on the instruction, the recording device 1 selects a deodorization portion to be replaced (step S12). Specifically, the recording device 1 specifies whether the target of the operation of replacing the deodorization unit 40 is the first deodorization portion 20 or the second deodorization portion 50, and selects the specified deodorization portion as the deodorization portion to be replaced.

The recording device 1 moves the carriage 89 and the main frame 71 in accordance with the deodorization portion selected in step S12 (step S13). That is, the frame moving motor 61 and the carriage driving motor 87 are operated by the control unit 101.

The operation in step S13 will be described in detail. In a case where the first deodorization portion 20 is selected, the recording device 1 moves the carriage 89 and the main frame 71 to a position at which replacement of the deodorization unit 40 in the first deodorization portion 20 is facilitated. Specifically, the recording device 1 moves the carriage 89 in a +X direction. Accordingly, the carriage 89 moves to a side away from the first deodorization portion 20 in the direction along the X-axis. At this time, the recording device 1 moves the carriage 89 to at least the recording range R2. Here, the recording device 1 may move the carriage 89 up to the end of the +X side of the range R1. Furthermore, the recording device 1 moves the main frame 71 to the rear side such that the main frame 71 deviates from above the first deodorization portion 20. Preferably, the recording device 1 moves the main frame 71 along the Y-axis to the rearmost position in a range in which the main frame 71 can move.

In a case where the second deodorization portion 50 is selected, in step S13, the recording device 1 moves the carriage 89 and the main frame 71 to a position at which replacement of the deodorization unit 40 in the second deodorization portion 50 is facilitated. Specifically, the recording device 1 moves the main frame 71 to the front side such that the main frame 71 deviates from the second deodorization portion 50. Preferably, the recording device 1 moves the main frame 71 along the Y-axis to the foremost position in a range in which the main frame 71 can move. As a result, in a state in which the front surface cover 11 is opened, the user can easily insert his/her hand into the housing 10 from the front surface of the recording device 1 and perform an operation on the second deodorization portion 50. Furthermore, in a case where the second deodorization portion 50 is selected, the recording device 1 may move the carriage 89 to the left end of the range R1.

After moving the carriage 89 and the main frame 71 in step S13, the recording device 1 notifies the user that the movement of the carriage 89 and the movement of the main frame 71 has been completed (step S14). The notification in step S14 is performed by, for example, the control unit 101 causing the touch panel 12 to display characters or images.

The recording device 1 stands by until the user inputs the start of the operation of replacing the deodorization unit 40 by operating the touch panel 12 (step S15). In a case where the input of the operation start is received (step S15; YES), the recording device 1 proceeds to step S16. In step S16, the recording device 1 displays a guide such as an operation procedure on the touch panel 12, and stops the error detection. The guide displayed on the touch panel 12 by the recording device 1 in step S16 includes, for example, images and characters for explaining the order and method of the operation of replacing the deodorization unit 40. The guide displayed on the touch panel 12 in step S16 is a guide for the operation for the deodorization portion selected in step S12.

In Step S16, the recording device 1 may stop detection of cover errors for all covers included in the recording device 1 and deodorization portion errors related to all the deodorization portions included in the recording device 1. All the covers include, for example, the front surface cover 11 and the side surface cover 14, and all the deodorization portions include the first deodorization portion 20 and the second deodorization portion 50.

Furthermore, in step S16, the recording device 1 may 1 may stop detection of the deodorization portion error of the deodorization portion selected in step S12 and detection of the cover error of the cover related to the selected deodorization portion. For example, in a case where the first deodorization portion 20 is selected, the recording device 1 may stop the detection of the deodorization portion error related to the first deodorization body sensor 28a and the first lid sensor 28b and the detection of the cover error of the side surface cover 14 in step S16. In this case, the recording device 1 does not stop the function of detecting the deodorization portion error related to the second deodorization body sensor 58a and the second lid sensor 58b and the cover error of the front surface cover 11. In the same manner, in a case where the second deodorization portion 50 is selected, the recording device 1 may 1 may stop the detection of the deodorization portion error related to the second deodorization body sensor 58a and the second lid sensor 58b and the detection of the cover error of the front surface cover 11 in step S16. In this case, the recording device 1 does not stop the function of detecting the deodorization portion error related to the first deodorization body sensor 28a and the first lid sensor 28b and the cover error of the side surface cover 14.

The recording device 1 determines whether or not the cover is closed (step S17), and waits while the cover is not closed (step S17; NO). In a case where it is determined that the cover is closed (step S17; YES), the recording device 1 proceeds to step S18. The cover to be determined in step S17 is a cover corresponding to the deodorization portion selected in step S12. Specifically, the cover is one of the side surface cover 14 corresponding to the first deodorization portion 20 and the front surface cover 11 corresponding to the second deodorization portion 50. In step S17, the recording device 1 may stand by until all the covers included in the recording device 1 are closed. The determination in step S17 is performed using one or more detection values of the front surface cover sensor 11c and the side surface cover sensor 14c.

In step S18, the recording device 1 acquires the detection value of a sensor included in the deodorization portion selected in step S13 (step S18). For example, in a case where the first deodorization portion 20 is selected in step S12, the recording device 1 acquires the detection values of the first deodorization body sensor 28a and the first lid sensor 28b in step S18. The same applies to a case where the second deodorization portion 50 is selected in step S12.

The recording device 1 determines whether or not the deodorization portion is in a normal state based on the detection value acquired in step S18 (step S19). The normal state is a state in which the lid portion is closed and the deodorization unit 40 is attached. For example, in the first deodorization portion 20, the lid portion 23 is closed and the deodorization unit 40 is accommodated in the accommodation portion 21.

In a case where it is determined that the deodorization portion is not in the normal state (step S19; NO), the recording device 1 notifies an operation failure (step S20) and returns to step S18. The notification in step S20 is performed by, for example, the control unit 101 causing the touch panel 12 to display characters or images for requesting confirmation of the state of the deodorization portion.

In a case where it is determined that the deodorization portion is in the normal state (step S19; YES), the recording device 1 ends this processing.

5. Other Embodiments

The above-described embodiment is merely a specific example to which the present disclosure is applied. The present disclosure is not limited to the configuration of the above-described embodiment, and can be implemented in various aspects without departing from the gist of the disclosure.

For example, in the above-described embodiment, a configuration in which the recording device 1 includes the first deodorization portion 20 and the second deodorization portion 50 has been described, but this is an example. For example, the recording device 1 may include three or more deodorization portions.

Furthermore, for example, in the above-described embodiment, a configuration in which the first deodorization portion 20 discharges air downward through the duct 29 and the second deodorization portion 50 discharges air downward through the duct 59 has been described. In this configuration, the air discharged from the first deodorization portion 20 and the air discharged from the second deodorization portion 50 are discharged toward the bottom plate 13 inside the housing 10. This is an example, and for example, the first deodorization portion 20 may include the duct 29 coupled to the outside of the housing 10, and may be configured to discharge air to the outside of the housing 10 through the duct 29. The same applies to the second deodorization portion 50.

Furthermore, in the above-described embodiment, a locking mechanism for locking the front surface cover 11 and/or the side surface cover 14 may be provided. For example, a first cover locking mechanism for fixing the front surface cover 11 in a state of being closed and locking the front surface cover 11 so as not to be opened may be provided. Furthermore, a second cover locking mechanism for fixing the side surface cover 14 in a state of being closed and locking the side surface cover 14 so as not to be opened may be provided. The first cover locking mechanism and the second cover locking mechanism may be coupled to the control unit 101 and configured to be perform locking and unlocking under the control of the control unit 101. In this case, the control unit 101 may perform control of locking the first cover locking mechanism and the second cover locking mechanism while the recording device 1 is performing recording on the medium M and control of unlocking the first cover locking mechanism and the second cover locking mechanism after the recording on the medium M is completed.

Furthermore, in the above-described embodiment, a configuration in which the table 31 on which the medium M is placed does not move in the direction along the X-axis and the direction along the Y-axis and the carriage 89 moves has been described as an example. A target to which the present disclosure is applied is not limited to the configuration of the present embodiment. For example, it is of course possible to apply the present disclosure to the recording device that moves the medium M in at least one of the direction along the X-axis or the direction along the Y-axis when the recording is performed on the medium M.

The configurations illustrated in FIGS. 1 to 7 and the functional configuration illustrated in FIG. 8 are examples of the recording device 1, and the target to which the present disclosure is applied is not limited to the configuration illustrated in each drawing. For example, the recording device 1 may include configuration units not illustrated in FIG. 8.

Furthermore, in a case where the operation of the recording device 1 described above is realized by using a processor included in the control unit 101, a program to be executed by the processor can be configured in a form of a recording medium or a transmission medium that transmits the program. As the recording medium, a magnetic or optical recording medium or a semiconductor memory device can be used. The recording medium may be an internal storage device included in the server device.

The steps of the operation illustrated in FIG. 9 is divided according to main processing contents in order to facilitate understanding of the operation of the recording device 1, and are not limited by the way of division of the processing and the name thereof. The processing may be divided into more steps according to the processing contents. One step may be divided so as to include more processing. The order of the steps may be changed as appropriate.

6. Configuration Described in Embodiment

The following configurations will be described based on the above-described embodiment.

Configuration 1

A recording device including a medium support portion that supports a medium, a recording unit configured to perform recording on the medium, an irradiation unit configured to emit an ultraviolet ray toward the medium, a deodorization portion configured to perform deodorization, and a housing configured to accommodate the medium support portion, the recording unit, the irradiation unit, and the deodorization portion, in which the deodorization portion includes a deodorization body, a deodorization body cover that covers the deodorization body, and an accommodation portion that accommodates the deodorization body covered by the deodorization body cover, and the deodorization body is removable from the accommodation portion together with the deodorization body cover.

In the recording device according to Configuration 1, it is possible to take out the deodorization body accommodated in the accommodation portion from the deodorization portion. Therefore, the deodorization body can be replaced without removing the deodorization portion from the recording device. Since the deodorization body is covered by the deodorization body cover, the user can replace the deodorization body without directly touching the deodorization body with his/her hand. Therefore, the deodorization body of the recording device can be easily replaced, and the effect of reducing or removing the odor inside the housing can be maintained.

Configuration 2

The recording device according to Configuration 1, in which the housing includes a first opening through which at least a part of the deodorization portion is exposed, and includes a first cover that closes the first opening, and the first cover constitutes at least a part of a first surface constituting the housing.

In the recording device according to Configuration 2, the deodorization body can be replaced from the outside of the housing of the recording device by opening the first cover.

Configuration 3

The recording device according to Configuration 2, in which the housing includes a second opening through which the medium is placeable at the medium support portion and removable from the medium support portion, and includes a second cover that closes the second opening, and the second cover constitutes at least a part of a second surface different from the first surface in surfaces constituting the housing.

In the recording device according to Configuration 3, it is possible to open the first opening for replacing the deodorization body separately from the second opening for placing the medium at the medium support portion and taking out the medium from the medium support portion. Therefore, the deodorization body can be replaced without opening the second cover. Since the first opening is not related to the placing and removing of the medium, the first opening is only required to have a size corresponding to the deodorization body. Therefore, by providing the first opening having the size with which the deodorization body can be easily replaced, the deodorization body can be more easily replaced.

Configuration 4

The recording device according to Configuration 3, in which the accommodation portion includes a lid portion, and the deodorization body is removable from the accommodation portion together with the deodorization body cover by opening the lid portion.

In the recording device according to Configuration 4, it is possible to easily take out the deodorization body from the deodorization portion.

Configuration 5

The recording device according to Configuration 4, in which the lid portion is constituted by coupling a plurality of lid members in a foldable manner.

In the recording device according to Configuration 5, it is possible to easily open and close the lid of the deodorization portion even in a configuration in which a large space cannot be secured around the deodorization portion.

Configuration 6

The recording device according to Configuration 4 or Configuration 5, further including a first sensor configured to detect whether or not the first cover is closed, a second sensor configured to detect whether or not the second cover is closed, a lid portion sensor configured to detect whether or not the lid portion is closed, a deodorization body sensor configured to detect whether or not the deodorization body is accommodated in the accommodation portion, and a control unit configured to acquire detection states of the first sensor, the second sensor, the lid portion sensor, and the deodorization body sensor.

In the recording device according to Configuration 6, the control unit can manage whether or not the deodorization body is appropriately accommodated in the deodorization portion, whether or not the lid of the deodorization portion is closed, and whether or not the opening and closing portion of the housing of the recording device is closed. Therefore, it is possible to prevent the recording device from executing recording in an inappropriate state.

Configuration 7

The recording device according to Configuration 6, further including a notification unit, in which the control unit causes the notification unit to perform notification when the first cover or the second cover is closed in a state in which it is detected that the deodorization body is not accommodated in the accommodation portion or the lid portion is not closed.

In the recording device according to Configuration 7, it is possible to prevent the recording device from executing recording in an inappropriate state, and to prompt the user to correct the inappropriate state.

Configuration 8

The recording device according to any one of Configurations 4 to 7, in which an incombustible material is disposed on a surface of the accommodation portion except the lid portion.

In the recording device according to Configuration 8, since it is possible to effectively suppress the risk of fire in the deodorization portion, it is possible to use a combustible material such as activated carbon as the deodorization body.

Configuration 9

The recording device according to any one of Configurations 4 to 7, in which an incombustible material is disposed on the lid portion of the accommodation portion.

In the recording device according to Configuration 9, since it is possible to effectively suppress the risk of fire in the deodorization portion, it is possible to use a combustible material such as activated carbon as the deodorization body.

What is claimed is:

1. A recording device comprising:
a medium support portion configured to support a medium;
a recording unit configured to perform recording on the medium;

an irradiation unit configured to emit an ultraviolet ray toward the medium;
a deodorization portion configured to perform deodorization; and
a housing configured to accommodate the medium support portion, the recording unit, the irradiation unit, and the deodorization portion, wherein
the deodorization portion includes a deodorization body, a deodorization body cover that covers the deodorization body, and an accommodation portion that accommodates the deodorization body covered by the deodorization body cover, and the deodorization body is removable from the accommodation portion together with the deodorization body cover,
wherein, the housing includes a first opening through which at least a part of the deodorization portion is exposed, and includes a first cover that closes the first opening, and the first cover constitutes at least a part of a first surface constituting the housing,
the housing includes a second opening through which the medium is placeable at the medium support portion and removable from the medium support portion, and includes a second cover that closes the second opening, and the second cover constitutes at least a part of a second surface different from the first surface of surfaces constituting the housing,
the accommodation portion includes a lid portion, and the deodorization body is removable from the accommodation portion together with the deodorization body cover by opening the lid portion,
the lid portion is constituted by coupling a plurality of lid members in a foldable manner,
a first sensor configured to detect whether or not the first cover is closed, a second sensor configured to detect whether or not the second cover is closed, a lid portion sensor configured to detect whether or not the lid portion is closed, a deodorization body sensor that detects whether or not the deodorization body is accommodated in the accommodation portion, and a control unit that acquires detection states of the first sensor, the second sensor, the lid portion sensor, and the deodorization body sensor, and
a notification unit, wherein the control unit causes the notification unit to perform notification when the first cover or the second cover is closed in a state in which it is detected that the deodorization body is not accommodated in the accommodation portion or the lid portion is not closed.

2. The recording device according to claim 1, wherein the lid portion is constituted by coupling a plurality of lid members in a foldable manner.

3. The recording device according to claim 1, wherein an incombustible material is disposed at a surface of the accommodation portion except the lid portion.

4. The recording device according to claim 1, wherein an incombustible material is disposed on the lid portion of the accommodation portion.

* * * * *